(12) United States Patent
Flock et al.

(10) Patent No.: US 6,353,753 B1
(45) Date of Patent: Mar. 5, 2002

(54) OPTICAL IMAGING OF DEEP ANATOMIC STRUCTURES

(76) Inventors: Stephen Thomas Flock, 13836 W. 66th Dr., Arvada, CO (US) 80004; Kevin Scott Marchitto, 14708 Ridgewood Dr., Little Rock, AR (US) 72211

( * ) Notice: Subject to any disclaimer, the term of this patent is extended or adjusted under 35 U.S.C. 154(b) by 0 days.

(21) Appl. No.: 09/305,418

(22) Filed: May 5, 1999

Related U.S. Application Data

(60) Provisional application No. 60/084,283, filed on May 5, 1998, now abandoned.

(51) Int. Cl.$^7$ ................................................ A61B 6/00
(52) U.S. Cl. ....................................................... 600/473
(58) Field of Search ................................ 600/407, 473, 600/476, 477, 420; 382/128, 130, 131, 132, 254, 260, 263, 274

(56) References Cited

U.S. PATENT DOCUMENTS

| 4,817,622 A | | 4/1989 | Pennypacker | 128/664 |
|---|---|---|---|---|
| 5,465,718 A | * | 11/1995 | Hochman et al. | 600/420 |
| 5,519,208 A | | 5/1996 | Esparza | 250/226 |
| 5,730,133 A | * | 3/1998 | Godik | 600/407 |
| 5,854,851 A | * | 12/1998 | Bamberger et al. | 382/132 |

FOREIGN PATENT DOCUMENTS

| WO | WO96/39925 | 12/1996 | A61B/5/00 |
|---|---|---|---|
| WO | WO99/37980 | 7/1999 | G01J/4/00 |

OTHER PUBLICATIONS

C. J. Gostout & S. L. Jacques, Infrared Video Imaging of Subsurface Vessels: a Feasibility Study for the Endoscopic Management of Gastrointestinal Bleeding. *Gastrointestinal Endoscopy*, vol. 41, No. 3, pp. 218–224 (Mar. 1995).

M. Rajadhyaksha, et al., In vivo Confocal Scanning Laser Microscopy of Human Skin; Melanin Provides Strong Contrast. *J. Invest Dermatol.* vol. 104, pp. 946–952 (1995).

G. A. Bellotti, et al., Fiberoptic Transillumination for Intravenous Cannulation under General Anesthesia. *Anesthesia and Analgesia*, vol. 60, No. 5, pp. 348–351 (May 1981).

P. M. Wall & L. R. Kuhns, Percutaneous Arterial Sampling Using Transillumination. *Pediatrics*, vol. 59, pp. 1032–1035 (1977).

L. R. Kuhns, et al., Intense Transillumination for Infant Venipuncture. *Radiology*, vol. 116, pp. 734–735 (Sep. 1975).

J. S. Curran & W. Ruge, A Restraint and Transillumination Device for Neonatal Arterial/Venipuncture: Efficacy and Thermal Safety. *Pediatrics*, vol. 66, No. 1, pp. 128–130 (Jul. 1980).

N. Hayashi, et al., Identification and Diameter Assessment of Gastric Submucosal Vessels using Infrared Electronic Endoscopy. *Endoscopy*, vol. 26, pp. 686–689 (1994).

M. Dinner, Transillumination to Facilitate Venipuncture in Children. *Anesthesia and Analgesia*, vol. 74, p. 467 (1992).

* cited by examiner

Primary Examiner—George Manuel
(74) Attorney, Agent, or Firm—Benjamin Aaron Adler (57) ABSTRACT

The present invention provides apparatus and means for visualizing blood vessels and subsurface anatomic structures during surgery and in real time with improved optical imaging and minimized trauma to the patient. More specifically, the present invention provides a method for imaging a deep anatomic tissue of interest, comprising the steps of: emitting radiant energy to the surface of said tissue; enhancing contrast of said radiant energy; and detecting reflected radiant energy from said tissue surface, wherein said reflected radiant energy provides imaging information of said tissue.

30 Claims, 4 Drawing Sheets

OPTICAL IMAGING OF DEEP ANATOMIC STRUCTURES

CROSS-REFERENCE TO RELATED APPLICATION

This patent application claims benefit of provisional patent application U.S. Ser. No. 60/084,283, filed May 5, 1998, now abandoned.

BACKGROUND OF THE INVENTION

1. Field of the Invention

The present invention relates generally to the fields of optical imaging and medical treatment. More specifically, the present invention relates to an apparatus and means for improved optical imaging of deep anatomic structures.

2. Description of the Related Art

Visualization of anatomical components that reside beneath the skin, or deep in body cavities, is a complex medical problem. Though endoscopy has revolutionized certain aspects of surgery on such components, certain risks are still apparent. Among these, the risk of accidentally cutting a vein or artery that lies near the treatment volume is very high, and places the patient's life in jeopardy. Such blood vessels may be invisible to the endoscopic surgeon using regular (white light) illumination due to the relatively opaque nature of biological tissues.

Setting intravenous (IV) lines and venipuncture procedures are often very difficult in geriatric or pediatric patients, as well as in obese patients or patients with a great deal of scar tissue. This is a particular problem in diabetics and chemotherapy patients where damage to the skin resulting from numerous needle sticks makes the blood vessels difficult to locate.

Imaging deep anatomical structures with radiant energy has not been possible due to the excessive scatter and absorption of photons, and thus the relatively short mean-free-path between scattering and/or absorbing interactions. The consequence of this is that photons transmitted through, or reflected from, tissue and anatomic structures have suffered excessive scattering events and thus carry little or no useful image information. On the other hand, few photons that are singularly scattered escape from the tissue, thus limiting the effectiveness of real-time imaging. Ideally, therefore, in order to quickly accumulate image information on deep anatomical structures, one must reduce or eliminate both singularly and excessively scattered photons from the image.

The prior art is deficient in the lack of effective means of imaging deep anatomical structures with radiant energy. The present invention fulfills this long-standing need and desire in the art.

SUMMARY OF THE INVENTION

The present invention is directed to an apparatus and means for visualizing blood vessels and subsurface anatomic structures during surgery and in real time, in humans and animals, which will improve the success rate of medical procedures and minimize any trauma to the patient.

In one embodiment of the present invention, there is provided a method for imaging deep anatomic structures of tissue of interest, comprising the steps of emitting radiant energy to the surface of the tissue; enhancing contrast of the radiant energy and then detecting the radiant energy reflected from the tissue surface, wherein the reflected radiant energy provides imaging information of the anatomic structures of the tissue. Preferably, the imaging method further comprises a step of administering an image enhancing agent to the tissue prior to the emission of radiant energy.

In another embodiment of the present invention, there is provided an apparatus for imaging deep anatomic structures, comprising a single or multiple source(s) for producing radiant energy; at least one contrast enhancing element and charge-coupled device video camera(s) with a means of focusing.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

In the present invention, the following terms have the definitions set forth below. Terms not defined specifically will have the meaning generally accepted by those having ordinary skill in this art.

As used herein, "mean-free path", "band-pass filter", "phase sensitive detection", "phase modulated detection", "scatter", "digital-delay pulse", "raster-scanning pattern", "charge-coupled device", "long-pass infrared filter", "linear polarizing filter", "circular polarizing filter", "gain control", and "black level control" shall take the usual definitions used by people skilled in the art of optics and/or biomedical optics.

As used herein, "depth dependent information" and "depth discriminate information" shall refer to information that is a function of depth in tissue and is based on measuring photons.

As used herein, "source-detector temporal synchronization" shall refer to a photon source which is modulated in synchronicity with a photon detector.

As used herein, "off-axis light" shall refer to light that propagates on a vector that is not coincident with a line drawn along the axis of the detector to the surface of the tissue.

As used herein, "pixel-by-pixel" shall refer to a mathematical procedure done upon the same pixels (designated by their x-y coordinates on the CCD chip) in at least two digitized images (e.g. pixel number (114,198) in one imaged is subtracted from pixel number (114,198) in another image).

The present invention provides a source of radiant energy and imaging detector, which is configured to image subsurface anatomic structures. The source consists of a portable, 0.5 W continuous-wave 800 nm diode laser and power supply, while a second source consists of a 0.5 W continuous-wave 670 nm diode laser and power supply. The power supplies are modulated on and off by a digital-delay pulse generator. The output of the lasers is collimated with lenses and configured to impinge normally on skin with a spot size of about 1 mm. The laser beams are contained within a hollow tube, which is pressed up against the skin, and which serves to contain the beams for safety reasons to shield the imaging system from the bright spots where the lasers impinge on the skin.

Two charge-coupled device (CCD) video cameras with imaging optics are positioned in a way such that it can image the tissue around where the lasers impinge on the skin. Each camera has a 10 nm bandpass optical filter (with center wavelengths at 800 and 670 nm) in front of the objective optic. The output of the laser is sent to a frame grabber and video monitor. The frame grabber is triggered by the output of the digital-delay pulse generator which is synchronized to the laser sources. The lasers are sequentially modulated on and off, and the frame grabber is triggered such that images illuminated by each laser are digitized. The frame grabber/microcomputer takes the arithmetic difference of the images in real-time such that any difference between the images are emphasized.

Further real-time image processing is used to enhance contrast. A prior intravenous injection of Indocyanine Green would optionally enhance the contrast in blood vessels, if that is the structure of interest to be imaged. By linearly polarizing the laser light and placing a linear polarizer in front of the camera, further contrast can be added by rotating the camera polarizer until the image improves. Optionally incorporating this imaging methodology into an endoscope would not involve any further technology, only a decrease in size of some of the components optically active species.

The present invention is directed to apparatus and means of imaging deep anatomic structures with radiant energy.

In one embodiment of the present invention, there is provided a method for imaging deep anatomic structures of tissue of interest, comprising the steps of emitting radiant energy to the surface of the tissue; enhancing contrast of the radiant energy and then detecting the radiant energy reflected from the tissue surface, wherein the reflected radiant energy carries imaging information of the anatomic structures of the tissue. Optionally, the radiant energy is comprised of ambient light or a passive light source which may exist in proximity to the area of interest. Generally, the radiant energy is produced by a single or multiple source, such as an incandescent light source, an infrared light source, a LED, a quartz-halogen lamp and a Q-switched ruby laser. More preferably, the infrared light produced has a wavelength greater than 900 nm. Still preferably, the contrast is enhanced by one or more element(s). Representative examples of such contrast-enhancing elements include an infrared long-pass filter, a band-pass filter, a polarization filter and an adjustable black level control, wherein the element transmits radiant energy with a wavelength from 700 nm to 1000 nm. Furthermore, it is preferable that the reflected radiant energy is detected by charge-coupled device video camera(s) with imaging optics.

To further enhance the contrast, the imaging method disclosed herein comprises a step of administering an image enhancing agent to the tissue prior to the emission of radiant energy. Preferably, the image enhancing element is an absorbing or reflective dye. It can be a dye alone or a dye linked to certain substance(s). Representative examples are calcium-linked dye, iodine-linked dye, Indocyanine Green, dye-tagged antibodies, and graphite or graphite containing materials.

In another embodiment of the present invention, there is provided an apparatus for imaging deep anatomic structures, comprising a single or multiple source(s) for producing radiant energy; at least one contrast enhancing element and charge-coupled device video camera(s) with a means of focusing. Representative examples of the radiant energy-producing source include a n incandescent light source, an infrared light source, a LED, a quartz-halogen lamp and a Q-switched ruby laser. Still preferably, the contrast enhancing element is selected from the group consisting of an infrared long-pass filter, a band-pass filter, a polarization filter and a black level control. Further preferably, the charge-coupled device video camera has gain and/or black level controls, and the means of focusing is an optic lens.

The present invention is also directed to a method for imaging hemoglobin or myoglobin-containing anatomical structures, comprising the steps of: detecting reflected or transmitted radiant energy from an anatomical structures using a charge coupled device; and enhancing contrast of said radiant energy, wherein said radiant energy provides imaging information of said anatomical structures. Generally, the contrast is enhanced by at least one element selected from the group consisting of an infrared long-pass filter, a band-pass filter, a polarization filter, adjustable gain control and adjustable black level control. Preferably, the longpass filter transmits wavelengths greater than 900 nm and the bandpass filter transmits radiant energy with a wavelength between 700 nm to 1000 nm. In one aspect, the element is a manually or automatically adjustable black level control of greater than 150 mV.

The present invention is also directed to an apparatus for imaging deep anatomic structures, comprising: a charge-coupled device video camera(s) with a means of focusing; and at least one contrast enhancing element. Generally, the contrast enhancing element is selected from the group consisting of an infrared long-pass filter, a band-pass filter, a polarization filter, adjustable gain control and adjustable black level control. The black level control is preferably adjustable to greater than 150 mV. The contrast enhancing element is preferably an illumination device that emits two or more wavelengths. The means of illumination may use two or more wavelengths that are absorbed differentially by muscle and blood. This method may be used to image anatomical structures such as myoglobin or hemoglobin-containing tissues or fluids. Preferably, the contrast enhancing element is an illumination device that transmits radiant energy with a wavelength greater than 700 to 1000 nm. In one aspect, the contrast enhancing element is a bandpass filter with a center wavelength at or about 760, 880, 925 or 1000 nm. The charge coupled device video camera preferably has an enhanced spectral responsivity at wavelengths beyond 750 nm. The contrast enhancing element may use a digitizer or other means of image subtraction to remove background noise. Generally, the camera has a manually or automatically adjustable gain control greater than 10 db. Preferably, the contrast enhancing element is capable of measuring two or more wavelengths simultaneously. In one aspect, the means of focusing includes a magnification lens.

Preferably, the apparatus is positioned at an angle from radiant energy used to illuminate said anatomical target and the apparatus transmits a signal to a remote monitor.

The following examples are given for the purpose of illustrating various embodiments of the invention and are not meant to limit the present invention in any fashion.

EXAMPLE 1

Imaging Schema

Figure 1:
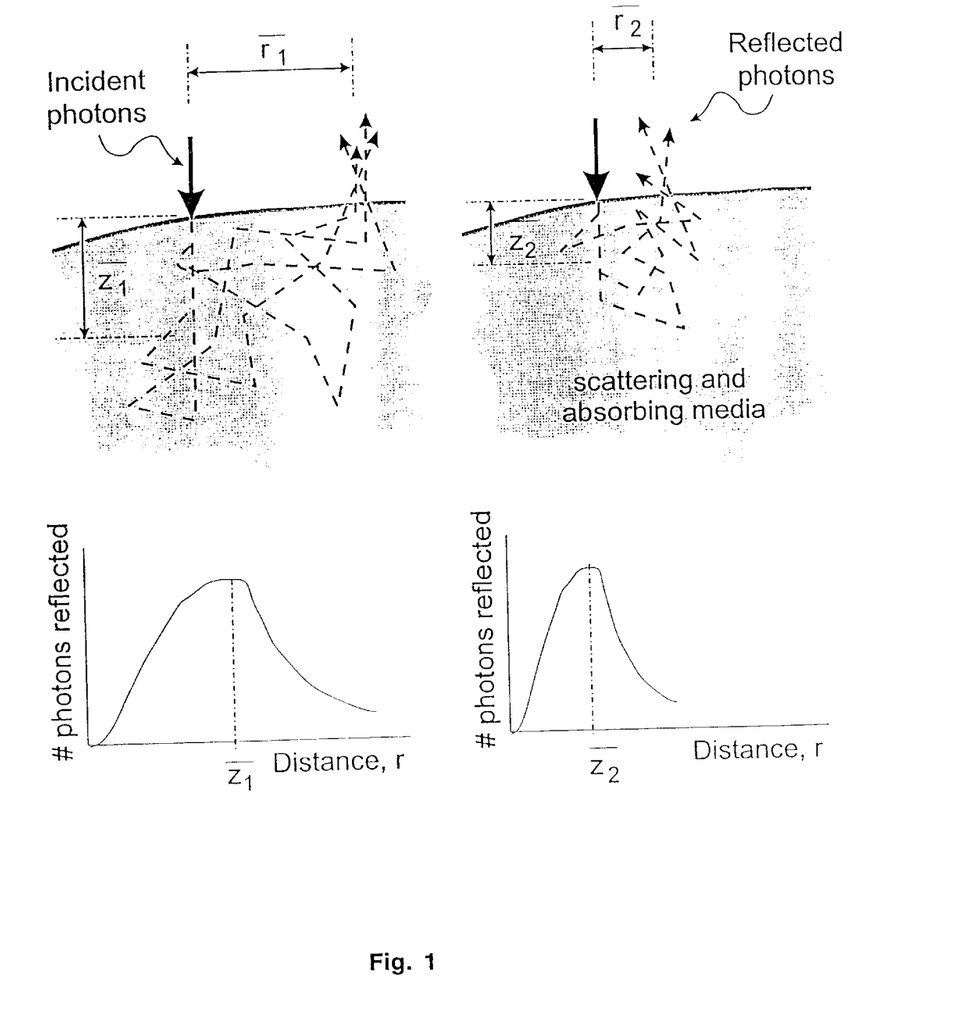
FIG. 1 is a diagram of scattered, reflected photon paths in media with two different sets of optical interaction coefficients.

There are several methods to capture photons which provide imaging (or chemical makeup) information from deep within tissue, and at user selectable depths within tissue. For example, FIG. 1 illustrates that photons of a single wavelength that are injected normally into tissue escape, on the average, at some distance, $\bar{r}_1$, from the site of photon injection. In a media with a shorter mean-free path, the average distance is less ($\bar{r}_2$). Furthermore, on the average, the photons escaping the tissue further away from the site of photon injection have penetrated to a greater depth, $\bar{z}$, than those escaping closer to the site of photon injection. Generally, for a tissue with a particular mean-free path, the depth dependent information carried by the escaping photons is a function of the distance, $\bar{r}$, from the site of photon injection. Thus, by capturing photons as a function of distance ($\bar{r}$), depth ($\bar{z}$) dependent imaging or spectral information is obtained.

Figure 2:
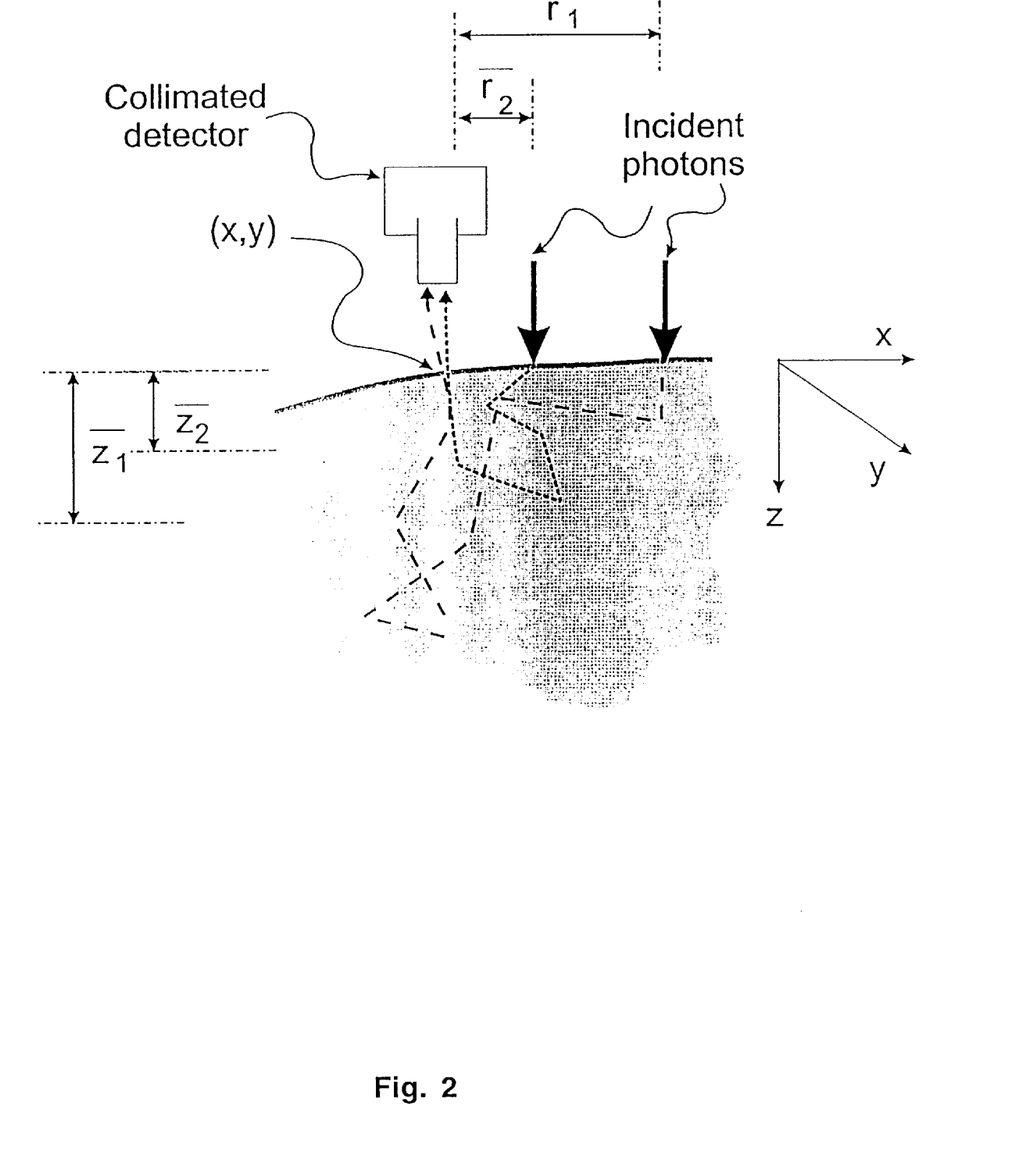
FIG. 2 is a diagram of imaged photons that were injected at two different points on the tissue surface.

Working the above mentioned method in reverse, one can inject photons of the same wavelength at two different distances, $\bar{r}_1$ and $\bar{r}_2$, from a detector which is collimated so as to collect only those photons escaping, on the average, as a particular x-y coordinate on the surface of the tissue and nearly normal to the surface (FIG. 2). In this case, the two photons carry different depth information, and so from these collected photons, depth discrimination is possible. By chopping the two incident photon beams at different frequencies, and using phase-locked detection, it is possible to discriminate at the detector between the photons which have travelled, on the average, to particular depths in the tissue. Various other schema are possible for discriminating the two photons beams; for example, each beam can consist of a pulse of radiant energy which is temporally synchronized to the detector.

Figure 3:
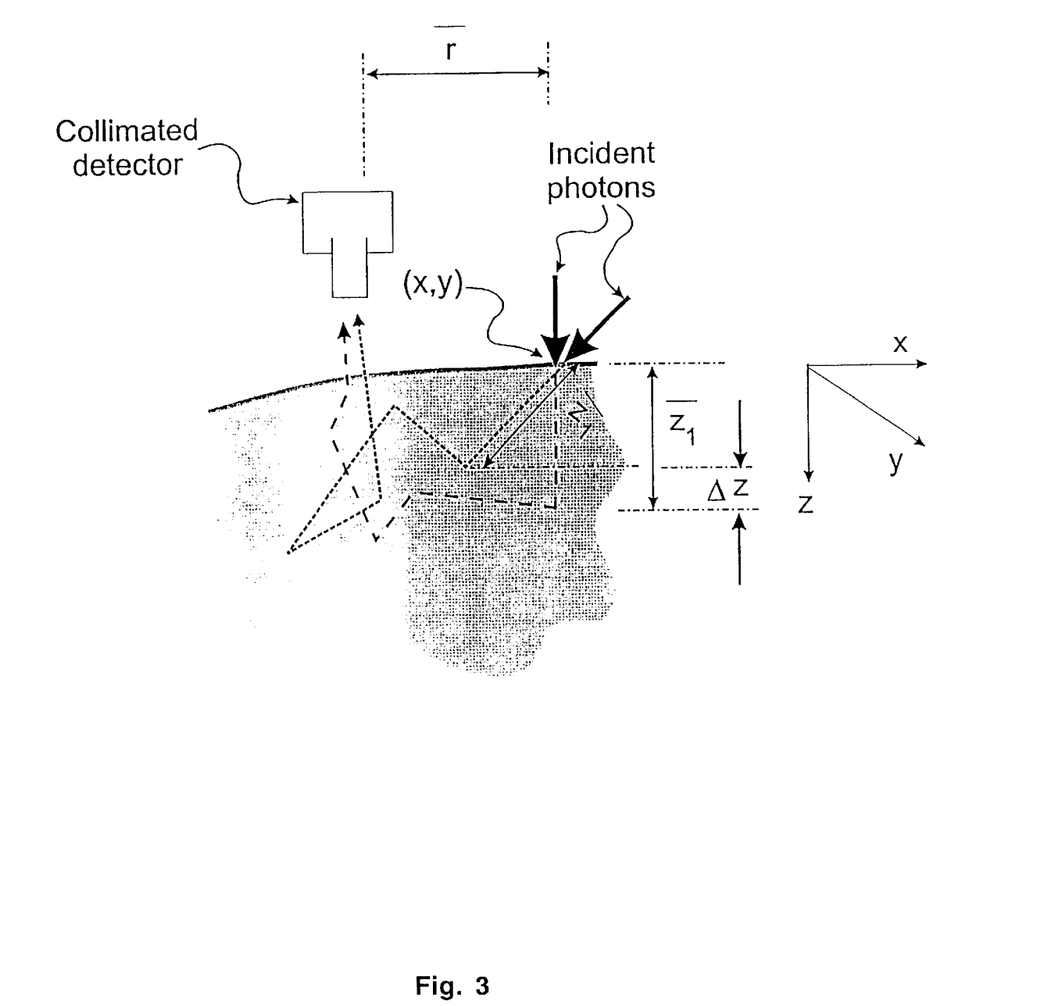
FIG. 3 is a diagram of imaged photons which were injected on the tissue surface at two angles with respect to the tissue surface.

By injecting photons of the same wavelength at the same (x, y) coordinate, but at different angles with respect to the surface of the tissue (FIG. 3), it is possible to discriminate depth information. These two photons beams propagate, on the average, the same distance in the tissue before being scattered or absorbed (i.e. the mean-free path $\bar{z}_1$). However, by virtue of the different injection geometries, the photons in each beam propagate, on the average, to two different depths, the difference of which is signified $\Delta z$. Thus, a detector can obtain different depth information when it can discriminate the source of the detected photons (which can be done using such techniques as phase-sensitive detection or source-detector temporal synchronization).

Figure 4:
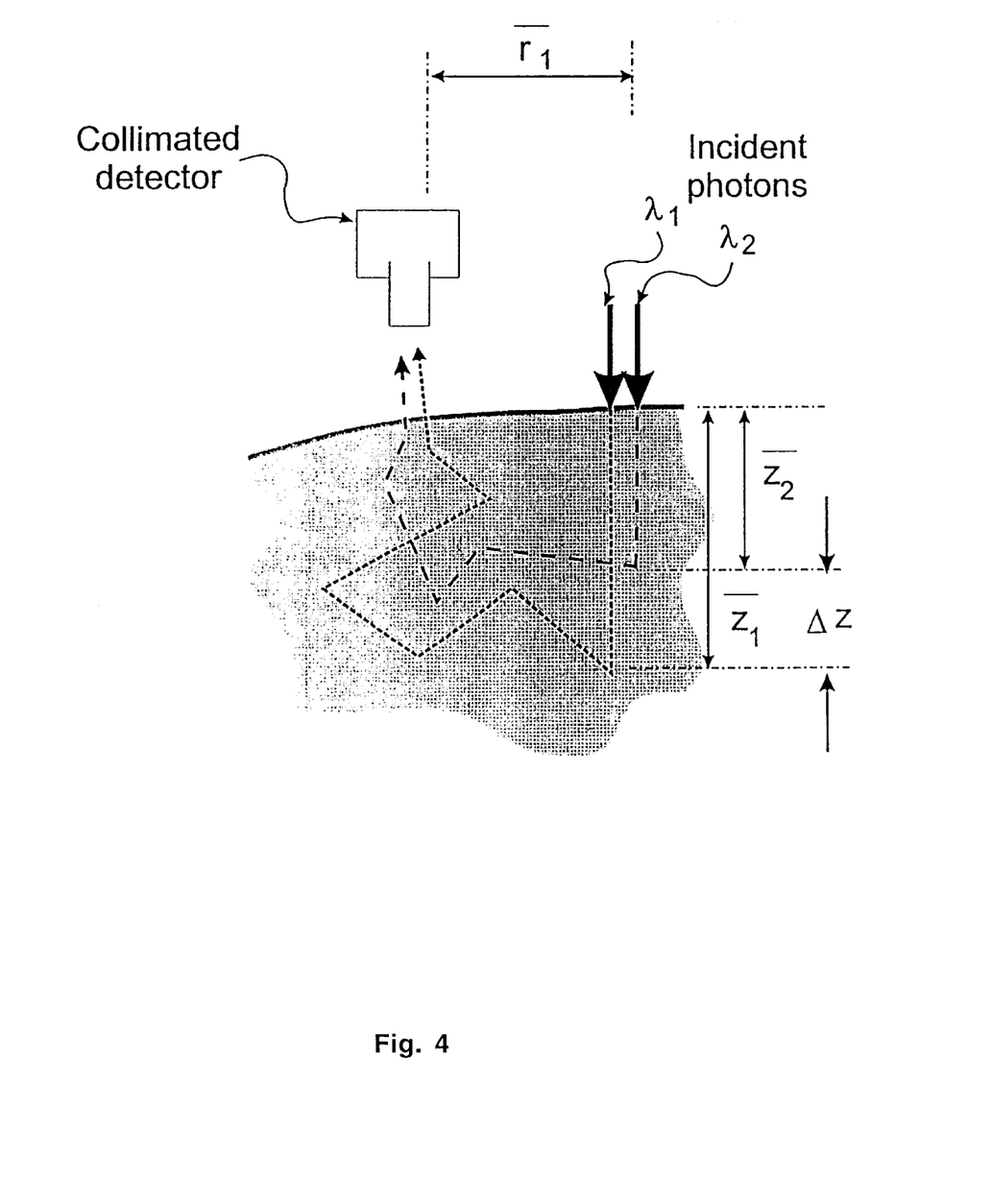
FIG. 4 is a diagram of imaged photons injected at the same point on the tissue surface, but which have two different wavelengths.

Depth discriminate information can be obtained using injected photons of differing wavelengths (FIG. 4). It is well known, for example, that radiant energy with a wavelength $\lambda_1$ of 1064 nm, for example, has a much larger mean-free path $\bar{z}_1$ in tissue than radiant energy with a wavelength $\lambda_2$ of 488 nm (mean-free-path $\bar{z}_2$), for example. Thus, by injecting beams of different wavelengths, and by detecting each separately (by, for example, using the previously stated techniques, or by using alternating bandpass filters with a center pass-band wavelength of $\lambda_2$ and $\lambda_1$ in front of the detector), depth discriminate information can be obtained. This concept can be extended to photons of differing states of polarization since the optical properties of tissue depend, to a degree, on the state of polarization of the incident photons.

The degree of detector collimation can affect how photons with a particular average depth of penetration, are collected. For example, a strongly collimated detector at a distance h from the surface of the tissue can be configured to collect photons which have propagated, on the average, through a particular region-of-interest (ROI). A less strongly collimated detector would collect photons that are less likely to have propagated only through the region of interest. Capturing the data and comparing the two sets of data allows one to focus on the region of interest and reject photons that carry information about the rest of the tissue. By increasing h, more specific photon discrimination results due to a small solid angle being subtended by the detector, albeit at the expense of capturing less total number of photons.

Collimation can be provided in a number of ways. Collimation by a physical collimator of a specific dimension and shape (e.g. a long, narrow tube) is one way, while a narrow-bandpass interferometric filter is another. In the case of the latter, any photons at the wavelength of the center of the passband, but that impinge on the filter element at non-normal incidence, will not be transmitted. Optionally, one may use optical elements that image a particular small area of the skin onto the detector, and which have light-absorbing baffles between the objective element and detector for absorbing off-axis light. Confocal techniques, which strongly reject photons that arise from tissue that is out of the volume of interest, can be used for photon discrimination (they have been used in microscopy, but not in photon discrimination of macroscopic objects such as blood vessels).

EXAMPLE 2

Altering Tissue Optical Properties: Dyes

Image enhancing agents may also be added to the system. These are small molecular weight dyes that can infused into the system thereby providing contrast or by fluorescing, thereby providing image information about the structure in which they are located. In one embodiment, a contrast agent is added to the system that has optical properties very different from the tissue in which it sequesters, thereby increasing the amount of scatter or absorption within the system and thereby altering the probability of photons escaping the system and being detected. Alternatively, dyes alone or linked to certain substances may preferentially be retained by organs or tissues. For example, calcium-linked dyes may sequester in the bone, iodine-linked agents often wind up in the thyroid, Indocyanine Green is retained in intact blood vessels, and dye-tagged antibodies will collect in tissues carrying specified antigens such as malignant or infected tissue. Graphite provides excellent contrast and appears black when visualized though the skin using the imaging schema described herein. Thus, imaging of the region of interest in tissue can be obtained using the aforementioned schema and contrast improving dyes or molecules.

EXAMPLE 3

Devices: Tissue Illuminators and Image Detectors

Illuminators are described which provide radiant energy that penetrates the skin or internal tissues. The radiant energy is either reflected or absorbed by anatomical structures, such as blood vessels, and a detector is used to analyze returning photons and the amount that has been absorbed.

Because the light is absorbed and scattered to a greater extent as it travels to deep tissues, and the reflected photons reaching a particular point (x, y, z) in space are a summation of photons multiply scattered from various parts of the tissue, one needs a means to improve contrast by discriminating against photons that do not carry significant image or spectral information. Due to the small mean-free-path of more radiant energy in tissue, transilluminated images made up of unscattered photons are usually impractical, while singularly scattered light will provide little or no information since it makes up only a small part of the transmitted and reflected radiant energy, carries little imaging information and cannot be distinguished from background noise easily.

When light from a single source is used to illuminate an object, little detail about its geometry in three dimensions can be obtained without complex evaluation of the scattered and reflected radiation returning from the object. Even with complex analysis, depth perception is limited by how finely one can calculate the degrees of scatter. To overcome this limitation, one of the inventions uses a multiple beam illuminator that emits infrared radiation that penetrates the skin from different angles. The reflected radiant energy thereby providing three-dimensional contrast as the photons move in different planes.

The use of multiple illuminators also provides comparative reference points by which one can subtract excess scatter which is determined by comparing rates at which photons return to a detector housed in the illuminator. Photons which are multiply scattered will be delayed to a greater extent than those experiencing minimal scatter. These multiply scattered photons will, after being reflected to the detector, result in an image of greater distortion. Therefore, as photons become more scattered, the image becomes "fuzzy." Some of the fuzziness may be subtracted by aiming two or more illuminators at the same target and differentially measuring the length of time photons from either source return to the detector. Differentiation occurs through the use of more than one wavelength or frequency. As the distance to a known reference point is constant, there should be an optimal amount of scatter that provides a true image.

EXAMPLE 4
Devices: Endoscopic Visualization

In another embodiment, a single or multiple source illuminator is encased in a catheter or endoscopic device. The illuminator may be composed of any infrared radiant energy source but preferably is a continuous-wave (cw) or pulsed laser with fiber optic leads that results in a lens at the distal end. The laser preferably produces infrared radiant energy which penetrates through surface tissues. When combined with infrared sensing devices, the apparatus allows the endoscopic or catheter operator to visualize subanatomical structures in great detail. For example, the device allows endoscopic surgeons to visualize blood vessels that are in danger of being accidentally incised during a procedure.

EXAMPLE 5
Means for Visualizing Blood Vessels

A charge-coupled device (CCD) video camera (available from Dage-MTI, Inc.) was fitted with a 25 mm focusing objective lens and was directed at the volar aspect of a volunteer's forearm. An infrared long-pass filter, which absorbs radiant energy at a wavelength less than about 750 nm (available from Edmund Scientific, Inc.) was positioned in front of the objective optic of the focusing lens. Illumination, in the form the radiant energy produced by a regular incandescent light source was directed at the forearm at approximately the same angle as the video camera. The output of the video camera was sent to a high resolution monochrome video monitor. Using this arrangement, blood vessels were visible in the forearm that were not visible under white-light illumination using the naked eye.

EXAMPLE 6
Improved Means for Visualizing Blood Vessels with a Long-Pass Infrared Filter The same arrangement as used in Example 5 was used, except that further contrast improvement resulted by positioning a long-pass infrared filter in front of the incandescent illumination.

EXAMPLE 7
Improved Means for Visualizing Blood Vessels with Further Enhanced Contrast by Linear Polarizers The same arrangement as used in Example 5 was used, except that a further contrast enhancing optical element consisting of an infrared transmitting linear polarizing filter (available from Edmund Scientific, Inc.) was positioned in front of the long-pass filter, and another identical linear polarizer was positioned in front of the light source whereby the axis of transmission was 90 degrees with respect to the polarizing positioned in front of the long-pass filter. The image produced by this arrangement had improved contrast as it is hypothesized that the specular reflection off the skin was reduced by the polarizing filters, and the contribution to the image of minimally scattered light (from very superficial layers of skin) was also reduced. Further contrast enhancement was obtained when an image was digitized with a polarizing filter in front of the long-pass filter oriented parallel to the polarizer in front of the illumination, and an image was digitized with a polarizing filter in front of the long-pass filter oriented perpendicular to the polarizer in front of the illumination, then a pixel-by-pixel difference of the two digitized images was calculated. The resulting image was normalized by the sum of the two digitized images. The final image had improved contrast as compared to any of the digitized single images.

EXAMPLE 8
Improved Means for Visualizing Blood Vessels with Further Enhanced Contrast by Circular Polarizers The same arrangement as used in Example 7 was used, except that the polarizing filters used were infrared transmitting circular polarizers (available from Edmund Scientific, Inc.). In this case, the each polarizer was oriented the same way. The image produced by this arrangement had improved contrast compared to the image without the polarizers in place.

EXAMPLE 9
Means for Visualizing Blood Vessels with an Optical Bandpass Filter The same arrangement as used in Example 5 was used, except that the contrast enhancing optical element consisted of an optical bandpass filter (available from Omega Optical, Inc.) with a full-width at half-maximum of 20 nm and a center wavelength of 800 nm. The image of the blood vessels appeared to have a higher contrast that obtained with an infrared long-pass filter was used as the contrast enhancing optical element.

EXAMPLE 10
Effects on Contrast Using the Means for Visualizing Blood Vessels The same arrangement used in Example 5 was used to study the effects on contrast of manually altering the gain and black level of the CCD video camera. In this case, it was determined that the contrast of the blood vessels was maximal when the black level was raised close to the white level (i.e. estimated to be near 1 volt) and the gain was increased (by about 20 decibels in one case). This process serves to increase the contrast between the blood vessels and the surrounding skin, which under regular illumination and observed with the naked eye, are either invisible or appear to have nearly identical optical densities. A similar observation was made when the gain and black level in the video camera was fixed, and an Argus 10 digital image processor (available from Hamamatsu, Inc.) was used to raise the lower pixel value (black) closer to the upper pixel value (white). In this case, it was necessary to increase the gain somewhat by opening the iris on the camera lens. Opening the iris too much, however, served to saturate the white features in the image whereupon contrast between the blood vessels and the tissue was actually decreased.

EXAMPLE 11

Variations in Applying the Means for Visualizing Blood Vessels

The same arrangement as used in Example 5 was used, except that the angle between the incident illumination and video camera was manually increased. The resulting images of blood vessels had improved contrast as compared to images obtained when the incident illumination and video camera were at approximately the same angle of incidence.

The same arrangement as used in Example 5 was used, except that the incident illumination was provided by either high-power GaAlAs (which emit at and around 880 nm) or GaAs (which emit at and around 940 nm) light-emitting diodes (available from Opto Diode Corp. and Newark Electronics, Inc.). When bandpass filters were used in conjunction with the LEDs instead of infrared long-pass filters, it was beneficial to use filters with a bandpass wavelength coincident with the LED emission wavelength.

A Smith-Nephew-Dyonics, Inc., quartz halogen light illuminator was coupled into an optical fiber bundle (Gemini, Inc.) and attached to a 4×155 mm focusing video arthroscope. A charge-coupled device (CCD) monochrome video camera with infrared longpass filter fixed in front of the CCD detector was attached to the focal plane of the arthoscope. The video output of the system was coupled into a high resolution color monitor (Panasonic, Inc.). The arthroscope was directed to the volar aspect of the forearm of a volunteer. The blood vessels were more easily visualized with this arrangement, than when the infrared long-pass filter was not positioned in front of the detector.

A charge-coupled device (CCD) video camera was fitted with a 25 mm focusing objective lens and was directed at the volar aspect of a volunteer's forearm. An infrared long-pass filter, which absorbs radiant energy at a wavelength less than about 750 nm (available from Edmund Scientific, Inc.) was positioned in front of the objective optic of the focusing lens. Illumination, in the form the radiant energy produced by a quartz-halogen lamp coupled into two cut-end optical fibers, was used. The ends of the fiber optics were gently pressed up against the skin at a spacing of about 1 cm and at an angle of about +45 and −45 degrees measured from the normal to the surface of the skin. The output of the video camera was sent to a high resolution monochrome video monitor. By manipulating the position of the optical fibers on the skin, it was possible to visualize subsurface blood vessels. The image of the blood vessel was of higher contrast that an image obtained with diffuse single source epi-illumination.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for imaging hemoglobin- or myoglobin-containing anatomical structures, comprising the steps of:

producing a source of radiant energy selected from the group consisting of an incandescent light source, an infrared light source, a LED, and a quartz-halogen lamp;

emitting said radiant energy to the surface of said hemoglobin- or myoglobin-containing anatomical structure;

detecting reflected radiant energy from said hemoglobin- or myoglobin-containing anatomical structure; and enhancing contrast of said radiant energy, wherein said reflected radiant energy provides imaging information of said hemoglobin- or myoglobin-containing anatomical structure.

2. The method of claim 1, wherein said infrared light source produces infrared light having a wavelength greater than 900 nm.

3. The method of claim 1, wherein said contrast is enhanced by at least one element selected from the group consisting of an infrared long-pass filter, a band-pass filter, a polarization filter, adjustable gain control and adjustable black level control.

4. The method of claim 3, wherein said element transmits radiant energy with a wavelength from 700 nm to 1000 nm.

5. The method of claim 3, wherein said element is a manually or automatically adjustable black level control of greater than 150 mV.

6. The method of claim 1, wherein said reflected radiant energy is detected by charge-coupled device video camera (s) with imaging optics.

7. The method of claim 1, further comprising a step of administering an image enhancing agent to said hemoglobin- or myoglobin-containing anatomical structure prior to said emitting of radiant energy.

8. The method of claim 7, wherein said image enhancing agent is a dye.

9. The method of claim 8, wherein said dye is selected from the group consisting of calcium-linked dye, iodine-linked dye, Indocyanine Green, dye-tagged antibodies and a graphite containing material.

10. An apparatus for imaging hemoglobin- or myoglobin-containing anatomical structures, comprising:

a source for producing radiant energy selected from the group consisting of an incandescent light source, an infrared light source, a LED, and a quartz-halogen lamp;

at least one contrast enhancing element; and a charge-coupled device video camera(s) with a means of focusing.

11. The apparatus of claim 10, wherein said contrast enhancing element is selected from the group consisting of a n infrared long-pass filter, a band-pass filter, a polarization filter, adjustable gain control and adjustable black level control.

12. The apparatus of claim 10, wherein said means of focusing is an optic lens.

13. A method for imaging hemoglobin or myoglobin-containing anatomical structures, comprising the steps of:
   detecting reflected or transmitted radiant energy from said hemoglobin- or myoglobin-containing anatomical structures using a charge coupled device; and
   enhancing contrast of said radiant energy, wherein said radiant energy provides imaging information of said anatomical structures.

14. The method of claim 13, wherein said contrast is enhanced by at least one element selected from the group consisting of an infrared long-pass filter, a band-pass filter, a polarization filter, adjustable gain control and adjustable black level control.

15. The method of claim 14, wherein said longpass filter transmits wavelengths greater than 900 nm.

16. The method of claim 14, wherein said bandpass filter transmits radiant energy with a wavelength between 700 nm to 1000 nm.

17. The method of claim 14, wherein said element is a manually or automatically adjustable black level control of greater than 150 mV.

18. The apparatus of claim 10, said apparatus comprising:
   a charge-coupled device video camera(s) with a means of focusing; and
   at least one contrast enhancing element.

19. The apparatus of claim 18, wherein said contrast enhancing element is a black level control that is adjustable to greater than 150 mV.

20. The apparatus of claim 18, wherein said contrast enhancing element is an illumination device that emits two or more wavelengths.

21. The apparatus of claim 18, wherein said contrast enhancing element is an illumination device that transmits radiant energy with a wavelength greater than 700 to 1000 nm.

22. The apparatus of claim 18, wherein said contrast enhancing element is a bandpass filter with a center wavelength at or about 760, 880, 925 or 1000 nm.

23. The apparatus of claim 18, wherein said charge coupled device video camera has an enhanced spectral responsivity at wavelengths beyond 750 nm.

24. The apparatus of claim 18, wherein said contrast enhancing element uses a digitizer or other means of image subtraction to remove background noise.

25. The apparatus of claim 14, wherein said camera has manually or automatically adjustable gain control greater than 10 db.

26. The apparatus of claim 18, wherein said contrast enhancing element is capable of measuring two or more wavelengths simultaneously.

27. The apparatus of claim 18, wherein said means of focusing includes a magnification lens.

28. An apparatus of claim 18, wherein said apparatus distinguishes between hemoglobin and myoglobin in said anatomical structure.

29. The apparatus of claim 18, wherein said apparatus is positioned at an angle from radiant energy used to illuminate said anatomical target.

30. The apparatus of claim 18, wherein said apparatus transmits a signal to a remote monitor.

* * * * *